United States Patent [19]

Friedman et al.

[11] Patent Number: 4,645,577

[45] Date of Patent: Feb. 24, 1987

[54] PRODUCTION OF CYANURIC ACID

[75] Inventors: Lester Friedman, Long Beach; Jock A. Hamilton, Los Angeles, both of Calif.

[73] Assignee: United Chemical Corporation, Los Angeles, Calif.

[21] Appl. No.: 109,358

[22] Filed: Jan. 3, 1980

[51] Int. Cl.$^4$ .................... C25B 3/00; C07D 251/32
[52] U.S. Cl. ...................................... 204/62; 544/192
[58] Field of Search .................. 544/192; 204/158 R, 204/62

[56] References Cited

U.S. PATENT DOCUMENTS 2,527,316 10/1950 Mackay .............................. 544/192
3,093,641 6/1963 Formaini ............................ 544/192

FOREIGN PATENT DOCUMENTS 00566 8/1979 Japan .................................. 544/192

OTHER PUBLICATIONS

Kirk-Othmer, Encyclopedia of Chemical Technology, pp. 563-586, 2nd ed.
Copson, Microwave Heating, AVI Publishing Company, Inc., Westport, Conn., 1962, pp. 372-373.

Primary Examiner—Henry R. Jiles
Assistant Examiner—Robert C. Whittenbaugh

[57] ABSTRACT

There is disclosed a method for the conversion of urea to cyanuric acid and cyclic by-products which comprises exposing urea in a liquid state to microwave radiation. Urea in liquid form, either molten anhydrous or in solution, is absorbent to microwave radiation, readily converting to cyanuric acid and cyclic by-products such as ammeline and ammelide. The desired products are substantially transparent to microwave radiation and the method thus avoids degradation of the desired products. Conversion of urea with microwave radiation also avoids the difficulties experienced with thermal decomposition that results from the poor thermal conductivity of the crude reaction products. The method thus permits conversion of urea in the form of a layer of urea directly to cyanuric acid and cyclic by-products.

10 Claims, No Drawings

PRODUCTION OF CYANURIC ACID

BACKGROUND OF THE INVENTION

1. Field of Invention

This invention relates to the preparation of cyanuric acid and, in particular, relates to the conversion of urea to cyanuric acid.

2. Brief Statement of the Prior Art

Cyanuric acid is prepared commercially by thermal decomposition of urea. Upon heating, urea forms biuret and triuret which cyclizes with evolution of ammonia and water into cyanuric acid and cyclic by-products such as ammeline and ammelide. The cyclic by-products can be readily hydrolyzed to cyanuric acid via acid or base hydrolysis.

The efficiencies of the prior thermal techniques are greatly impaired by the physical properties of the crude reaction product which is a mixture of cyanuric acid and the cyclic by-products. The crude reaction product solidifies at the reaction temperature, typically up to about 300° C., and the solidified mixture is an excellent thermal insulator. Increasing the temperature to improve the thermal heat transfer to the reaction mixture only results in depolymerization and degradation of the product.

Many techniques have been proposed to obviate or circumvent the problems presented by the physical nature of the reaction mixture. These techniques have included heating of urea in a particle form using a rotating kiln or a fluidized bed. Other techniques have suggested heating of urea on a molten bath of zinc, lead, or tin or dissolving the urea in an inert high boiling solvent such as propylene glycol. All of these techniques have some disadvantages; e.g., rotating kilns and fluidized beds present equipment and solids handling problems while solvents must be recovered from the reaction product.

BRIEF STATEMENT OF THE INVENTION

This invention comprises a method for the conversion of urea to cyanuric acid and cyclic by-products by exposure of urea in a liquid form to microwave radiation. The microwave radiation is electromagnetic radiation with a frequency from 900 to about 3,000 kiloHertz (kHz). In the preferred application, the urea is preheated to a temperature above its melting point and maintained at that temperature by the application of heat for a sufficient time to effect up to about 25–30% conversion of the urea. The molten and partially converted mixture is then applied as a layer on a belt or in trays and placed in or moved through a microwave oven for exposure therein to microwave radiation by batch or continuous processing. In the preferred embodiment, the molten, partially converted mixture is applied as a layer on a continuous belt of an industrial microwave oven and is transported through the oven by the belt. The layer of reaction mixture on the belt is exposed to microwave radiation within the oven cavity, to complete the conversion to the crude reaction products and solidify the reaction mixture. The crude reaction product is removed from the continuous belt as the belt exits from the microwave oven cavity. The crude reaction product is essentially cyanuric acid and cyclic by-products, and the latter can be readily converted to cyanuric acid by acid or base hydrolysis.

DESCRIPTION OF PREFERRED EMBODIMENTS

The invention comprises the conversion of urea and intermediate acyclic condensation products such as biuret and triuret to cyanuric acid and cyclic by-products such as ammeline and ammelide. The conversion is effected by exposing the urea and acyclic condensation products to microwave radiation. These reactants are absorbents of microwave radiation; i.e., electromagnetic radiation having a frequency from about 900 to about 3,000 kHz, when they are in the liquid state. The reactants can be liquified by heating to a molten condition and contacting substantially anhydrous molten urea and acyclic derivatives to the microwave radiation. Alternatively, the urea can be dissolved in a suitable solvent such as water or high boiling organic solvents.

The preferred method includes a pretreatment step wherein the urea is preheated to a molten condition, above its melting point of 132° C. Preferably, the urea is heated to a temperature of 160° to about 200° C., most preferably 180° to 190° C., and maintained at that temperature for a period of time, typically from 30 to about 300 minutes, preferably from 60 to about 180 minutes, to effect some conversion of the urea to intermediate and final products, typically to effect from 2 to about 40and preferably from 15 to about 30 percent conversion. This preheating step can be practiced in a stirred, jacketed vessel.

The molten and, preferably, partially converted urea is introduced into a microwave oven cavity and is exposed therein to microwave radiation to complete the conversion. The molten urea can be poured into trays which can be stacked in the oven in a batch treatment. Alternatively the treatment can be practiced continuously by moving the trays through the oven. It is preferred to transport the urea as a layer of molten urea on a traveling belt and, for this purpose, a woven fiberglass belt coated with Teflon has been used successfully. Since the microwave radiation readily penetrates into the melt, there is no significant limitation to the thickness of the melt in the oven, except as may be required by the mechanical limitations of the equipment. The melt can be moved through the microwave oven cavity at a rate sufficient to provide a residence time therein from about 2 to about 60 minutes, preferably from $3\frac{1}{2}$ to about 30 minutes. As the molten mixture progresses through the oven, the reaction and cyclization to cyanuric acid, ammeline, and ammelide occurs with concomitant formation of a porous, white solid. The reaction can be continued to substantially complete conversion of acyclic reactants such as urea, biuret, and triuret since there is no danger of degrading the desired products or discoloring the product as the cyclic products are substantially transparent to microwave radiation. Accordingly, the reaction can be run to substantially eliminate all water soluble acyclic reactants such as urea, biuret, and triuret and a crude reaction product substantially free of these components can be recovered at the outlet of the microwave oven. The microwave radiation can be from 900 to about 3,000 kHz. The two industry assigned microwave frequencies are 915 and 2450 kHz and either or both of these frequencies can be used in the oven.

The crude reaction product comprises chiefly cyanuric acid with lesser quantities of ammeline and ammelide. The latter can be converted to cyanuric acid by hydrolysis, using conventional techniques such as hydrolysis with aqueous sulfuric acid, typically sulfuric acid at a concentration of from 5 to about 20 weight percent at a temperature of from 90° to about 100° C. and for a period of time from 1 to about 3 hours which is sufficient to substantially convert all of the cyclic intermediate products to cyanuric acid. During the conversion, the ammonia which is liberated reacts with the sulfuric acid, forming ammonium sulfate.

The cyanuric acid product produced by this process is recoverable in a high degree of purity with substantially no presence of any degradation products. The product is a crystalline white powder that is recovered from the aqueous sulfuric acid in the hydrolysis step by settling and filtration and the like.

EXAMPLE I

The following example will illustrate a mode of practice of the invention and demonstrate results obtainable thereby.

The following experiments were performed in a household microwave oven having a 750-watt output. The urea used in the experiments was placed in a 10-inch square Pyrex tray, and in each experiment 150 grams of urea were employed. Urea prills were placed in the tray, melted and heated to about 190° C. The tray containing the clear melt was placed in the microwave oven and subjected to microwave radiation therein. The course of the reaction was observed. Ammonia and water were evolved and the molten urea was observed to become turbid and then to solidify after 9 minutes. After the urea had solidified, the radiation was stopped and the crude product was withdrawn and analyzed and found to contain 60–65 percent cyanuric acid.

The experiment was repeated; however, the urea was heated to a molten condition and thereafter the heating was continued at 190° C. until the melt became turbid. The melt was then placed in the microwave oven and subjected to microwave radiation until it solidified. Solidification of the melt occurred within 6.5 minutes. The microwave radiation was ceased, the product was removed and analyzed and found to comprise a mixture of about 65 percent cyanuric acid and 35 percent of a mixture of ammeline and ammelide. The total yield of the product mixture of cyanuric acid, ammeline and ammelide obtained in a series of experiments was from 78 to 87 percent of the theoretical yield.

In another experiment, approximately 5 weight percent N-methyl-pyrrolidone was added to the molten urea in the tray. The tray was placed in the microwave oven and observed during the application of microwave radiation. The clear melt evolved ammonia and water, became turbid, and solidified after 6.5 minutes. The reaction was then discontinued, and the tray contents were removed and cyanuric acid was recovered therefrom at a yield from 78 to 87 percent of theoretical as a mixture of approximately 65 percent cyanuric acid and 35 percent ammeline and ammelide.

In all the experiments, no attempt was made to recover urea from the volatiles released during the experiment. The difference of about 13 to 22 percent between the actual and theoretical yields comprises urea which is volatized during the experiments. In commercial practice, this urea can be readily recovered and recycled and the actual yield can become essentially quantitative.

EXAMPLE II

The conversion of urea to cyanuric acid is practiced in a commercial microwave oven having a continuous belt which passes over rollers in the oven cavity. The belt is fiberglass coated with Teflon. The reaction is effected by placing a layer of molten urea of about one inch on the belt and advancing the urea through the microwave oven. The belt velocity is controlled to provide a residence time from 10 to about 27 minutes in the microwave oven and the crude reaction product is recovered as a porous solid from the belt which exits from the microwave oven. The off gases from the oven are collected through a closed system and passed through a water scrubber to recover the ammonia and urea. The porous solid product is passed into a hammermill and pulverized and then is suspended as a slurry in aqueous sulfuric acid having a concentration of about 15 weight percent. The sulfuric acid slurry is maintained at a temperature of 95°–100° C. to hydrolyze the cyclic by-products to cyanuric acid. The sulfuric acid slurry is then permitted to settle and the solid cyanuric acid is recovered by settling, filtration, and washing.

In another run, the urea is preheated to a temperature of 160° to about 190° C. in a stirred vessel. The urea is maintained at the preheat temperature for about 30 to 180 minutes residence time to effect about 30 percent conversion of the urea. The preheated and partially converted molten reaction mixture is then placed on the belt and passed into the microwave oven. The product is recovered at a rate of production approximately 1½–2 times greater than that attained when using no preheat treatment.

In another run, solid urea prills are placed on the belt and moistened with a small amount of solvent such as water or N-methyl-pyrrolidone. The solvent permits the microwave radiation to melt the prills. After the melt is formed, dry prills are continuously added. This technique is the least efficient.

The invention has a number of advantages over prior processes. The solid crust of crude product that has thwarted thermal processes is no barrier to microwave adsorption by unconverted urea in the oven. Equipment formed or coated with Teflon, which is precluded from the thermal processes because of its poor heat conductivity, can be used to maximum advantage in the invention to present non-adhering surfaces to the crude reaction product. The high degree of transparency to microwave radiation of cyanuric acid and cyclic by-products insures decoupling of the energy application, thus providing an inherent curb to degradation of the desired product. Finally, the preferred process, which utilizes a thermal preheat, combines the advantages of both processes for maximum efficiency. The more thermodynamically efficient heating by conduction, convection, or thermal radiation can be used to its limit of incipient solidification of the melt and the remainder of the energy of reaction can be transferred by microwave radiation.

The invention has been described with reference to the illustrated and presently preferred mode of practice. It is not intended that the invention be unduly limited by this disclosure of preferred embodiments. Instead, it is intended that the invention be defined by the method steps and reagents, and their obvious equilavents, set forth in the following claims.

What is claimed is:

1. A method for conversion of urea to cyanuric acid and cyclic intermediate compounds which comprises: exposing urea in substantially anhydrous molten liquid state to microwave electromagnetic radiation having a frequency from 900 to 3,000 kHz.

2. A method for conversion of urea to cyanuric acid and cyclic intermediate compounds comprising the steps of preheating urea to a molten state and exposing the molten urea to microwave radiation having a frequency from 900 to 3,000 kHz.

3. The method of claim 2 wherein urea is preheated before exposure to said radiation.

4. The method of claim 3 wherein urea is preheated to a temperature from its melting point to about 200° C. before exposure to said radiation.

5. The method of claim 4 wherein urea is preheated to and maintained at a temperature from 160 degrees C. to about 200 degrss C. for a period of time sufficient to effect from 2 to about 40 percent conversion of the urea to cyanuric acid and intermediate compounds.

6. A method for conversion of urea to cyanuric acid and cyclic intermediate compounds which comprises: applying urea onto the surface of a moving conveyor belt as a melt, continuously transporting said belt into, through, and out of a microwave over cavity, thereby transporting said urea melt into said microwave oven cavity, exposing the urea on said belt to microwave radiation having a frequency from 90 to 3,000 kHz within said cavity and recovering a reaction product comprising cyanuric acid and cyclic by-products from said belt as it exits from said cavity.

7. A method for conversion of urea to cyanuric acid and cyclic intermediate compounds which comprises: applying solid urea onto the surface of a moving conveyor belt, initiating said method by moistening the urea with from 1 to 15 percent of a solvent, transporting said urea on said belt into said microwave oven cavity, exposing the urea to microwave radiation having a frequency from 900 to 3,000kHz within said cavity, discontinuing said step of moistening said urea after a molten layer of urea is established on the belt, and recovering a reaction product comprising cyanuric acid and cyclic by-products from said belt as it exits from said cavity.

8. The method of claim 5 wherein said preheating is conducted to effect from 15 to about 30 percent conversion of urea.

9. The method of claim 5 wherein said preheated and partially converted urea is applied as a molten layer onto a conveyor belt and transported into a mlcrowave oven cavity and exposed therein to said microwave radiation.

10. The method of claim 9 wherein a polytetrafluorethylene coated fiberglass belt is used to transport said urea through said microwave oven and a reaction product comprising cyanuric acid and cyclic by-products are removed from said belt.

* * * * *